(12) United States Patent
Fujihara et al.

(10) Patent No.: US 9,512,171 B2
(45) Date of Patent: Dec. 6, 2016

(54) FUNCTIONAL MOLECULE AND MANUFACTURING METHOD THEREFOR

(75) Inventors: Tsuyoshi Fujihara, Kawasaki (JP); Tomoyasu Kichise, Kawasaki (JP); Shozo Fujita, Kawasaki (JP)

(73) Assignee: APTA BIOSCIENCES LTD, Ledbury (GB)

( * ) Notice: Subject to any disclaimer, the term of this patent is extended or adjusted under 35 U.S.C. 154(b) by 1553 days.

(21) Appl. No.: 12/929,359

(22) Filed: Jan. 19, 2011

(65) Prior Publication Data

US 2011/0151510 A1 Jun. 23, 2011

Related U.S. Application Data

(60) Division of application No. 11/727,390, filed on Mar. 26, 2007, now abandoned, which is a continuation-in-part of application No. 11/585,888, filed on Oct. 25, 2006, now abandoned.

(30) Foreign Application Priority Data

Mar. 28, 2006 (JP) .................................. 2006-088802
Mar. 14, 2007 (JP) .................................. 2007-64602

(51) Int. Cl.
- *C40B 30/04* (2006.01)
- *C07K 1/107* (2006.01)
- *C07K 1/04* (2006.01)
- *C07K 1/22* (2006.01)

(52) U.S. Cl.
CPC ............... *C07K 1/1077* (2013.01); *C07K 1/04* (2013.01); *C07K 1/22* (2013.01)

(58) Field of Classification Search
None
See application file for complete search history.

(56) References Cited

U.S. PATENT DOCUMENTS

| | | |
|---|---|---|
| 5,475,096 A | 12/1995 | Gold et al. |
| 5,723,289 A | 3/1998 | Eaton et al. ............... 506/9 |
| 6,218,530 B1 * | 4/2001 | Rothschild et al. ........ 536/25.32 |
| 6,605,713 B1 * | 8/2003 | Furste ................. A61K 31/712 435/6.11 |
| 2002/0182597 A1 | 12/2002 | Kuimelis et al. |
| 2003/0027140 A1 | 2/2003 | Ju et al. |
| 2003/0143616 A1 | 7/2003 | Kuimelis et al. |
| 2004/0197841 A1 | 10/2004 | Apffel, Jr. .................... 435/7.92 |
| 2005/0079520 A1 | 4/2005 | Wu .................................. 435/6 |

FOREIGN PATENT DOCUMENTS

| | | |
|---|---|---|
| JP | 10-504719 | 5/1998 |
| JP | 2002-510505 | 4/2002 |
| JP | 2004-533608 | 11/2004 |
| WO | WO 96/06104 | 2/1996 |
| WO | WO 99/51773 | 10/1999 |
| WO | WO 02/079519 A1 | 10/2002 |
| WO | WO 2004/018081 A1 | 3/2004 |

OTHER PUBLICATIONS

Olejnik et al (1996 Nucleic Acids Research 24:361-6).*
Scaringe et al (1998 JACS 120:11820-1).*
Cho, S. et al., "Microbead-based affinity chromatography chip using RNA aptamer modified with photocleavable linker", *Electrophoresis*, 2004, vol. 25, p. 3730-3739.
J.C. Schulof et al.; "The final deprotection step in oligonucleotide synthesis is reduced to a mild and rapid ammonia treatment by using labile base-protecting groups"; *Nucleic Acids Research*; vol. 15; Nov. 2, 1987; pp. 397-416.

* cited by examiner

*Primary Examiner* — Christopher M Gross
(74) *Attorney, Agent, or Firm* — Kratz, Quintos & Hanson, LLP (57) ABSTRACT

A novel method for efficiently manufacturing a functional molecule with affinity for a target substance is provided along with a functional molecule manufactured by this method. The method for manufacturing a functional molecule includes binding, to a resin, a specific substance having a cleavable linker which is a site that is cleavable under a specific condition to prepare a specific-substance-bound resin, treating this specific-substance-bound resin with a solution comprising functional molecule candidates, and then cleaving the cleavable linker under the specific condition to select a functional molecule which has interacted specifically with the specific substance.

9 Claims, 5 Drawing Sheets

SEQ ID No. 9

GAAGGTGAAGGTCGGAGTCAAACG41G33G41G41C21C53G53CGCT43G45G44G45C13G44C53GGGAAATCCCATCACCATCTTC

1=dAleu-dA, 2=dAphe-dC, 3=dAglu-dT, 4=dGlys-dC, 5=dT-dAlys

FIG. 9

FUNCTIONAL MOLECULE AND MANUFACTURING METHOD THEREFOR

CROSS-REFERENCE TO RELATED APPLICATIONS

This application is a divisional of prior application Ser. No. 11/727,390, filed on Mar. 26, 2007, now abandoned, which is a continuation-in-part of prior application Ser. No. 11/585,888, filed on Oct. 25, 2006, now abandoned. This application is based upon and claims the benefit of priority from the prior Japanese Patent Application No. 2006-088802, filed on Mar. 28, 2006 and the prior Japanese Patent Application No. 2007-064602, filed on Mar. 14, 2007, the entire contents of which are incorporated herein by reference.

BACKGROUND OF THE INVENTION

1. Field of the Invention

The present invention relates to a comprehensive method for manufacturing functional molecules that exhibit high affinity for a variety of target substances, and that are particularly applicable to a wide range of fields including drugs, drug delivery, biosensors, controlling levels of gene expression, overcoming diseases caused by gene abnormalities or elucidating the functions of proteins translated through those genes, developing catalysts comparable to enzymes and the like. In the present invention, when a specific interaction can occur between a substance and a molecule the substance is called a target substance and the molecule is called a functional molecule. Interaction here includes physical adsorption and chemical adsorption as well as antigen-antibody reactions and other biological interactions. Affinity can be present when a specific interaction can occur.

2. Description of the Related Art

The complete human genome is already known. As a result, the attention of scientists has shifted to the analysis of the gene products, the proteins. It is not an exaggeration to say that in protein analysis, actual analysis of a protein can only be achieved by obtaining a functional molecule with affinity for that protein.

However, an extremely wide variety of proteins are contained in cells, and the sequences of many of them are unknown. The most common means of obtaining a functional molecule having affinity for a specific protein or other target substance is to select an affinity antibody using the immune system of an animal. Because animals are used in this method, however, a large quantity of protein is required, along with extensive procedures and costs. Another drawback has been that an affinity antibody to a specific substance is not produced.

One means for resolving such problems is the aptamer method (also called the Selex method), which does not rely on living animals {see, for example, U.S. Pat. No. 5,475,096 (Claims)}, but this method produces strong interactions only with certain proteins, and is not applicable to all proteins. The modified aptamer method has also been developed which uses a modified nucleic acid as a functional molecule, but only unmodified nucleic acids are produced via PCR, so this does not permit multiple selections as in the Selex method, and one problem has been how to effectively exclude non-specific interactions from a system containing multiple kinds of modified nucleic acids.

SUMMARY OF THE INVENTION

It is an object of the present invention to resolve these issues and provide a novel method of efficiently manufacturing a functional molecule with affinity for a target substance. Other objects and advantages of the present invention are made clear by the following explanation.

One aspect of the present invention provides a method for manufacturing a functional molecule, comprising: binding, to a resin, a specific substance having a cleavable linker that is a site that is cleavable under a specific condition to prepare a specific-substance-bound resin; treating the specific-substance-bound resin with a solution comprising functional molecule candidates; and cleaving the cleavable linker under the specific condition and selecting a functional molecule which has interacted specifically with the specific substance.

This aspect provides a novel method for efficiently manufacturing a functional molecule with affinity for a target substance.

In preferred embodiments, the specific substance is derived from at least one type of substance selected from proteins, lipoproteins, glycoproteins, polypeptides, lipids, polysaccharides, lipopolysaccharides, nucleic acids and drugs; the specific substance is derived from a protein; the functional molecule is a nucleic acid or modified nucleic acid; the functional molecule is a modified nucleotide n-mer (n≤2) comprising a modified nucleoside having a substituent group introduced into a nucleoside constituting a nucleic acid; the functional molecule can be transformed into a nucleic acid when the substituent group is removed by chemical treatment; the chemical treatment is alkali treatment; the cleavable linker is cleavable at 50° C. or less and in the pH range of 6.0 to 9.0; the cleavable linker has a disulfide bond or vicinal diol bond or is cleavable by light; the cleavable linker is a nucleic acid sequence cleavable by a restriction enzyme; and the cleavable linker is an amino acid sequence cleavable by an enzyme.

Another aspect of the present invention provides a functional molecule obtained by the aforementioned method. A novel functional molecule having affinity for a target substance is obtained by this aspect of the invention.

A novel method for efficiently manufacturing a functional molecule having affinity for a target substance and a novel functional molecule having affinity for a target substance are provided by the present invention.

DESCRIPTION OF THE PREFERRED EMBODIMENTS

Embodiments of the present invention are explained below using drawings, tables, formulae, examples and the like. These drawings, tables, formulae, examples and the like and explanations illustrate the present invention and do not limit its scope. Other embodiments may also be included in the scope of the present invention to the extent that they match the intent of the present invention.

The functional molecule manufacturing method of the present invention includes binding, to a resin, a specific substance having a cleavable linker which is a site that is cleavable under a specific condition to prepare a specific-substance-bound resin, treating the specific-substance-bound resin with a solution comprising functional molecule candidates, and then, cleaving the cleavable linker under the specific condition to select a functional molecule which has interacted specifically with the specific substance.

In this way, non-specific interactions can be controlled because there is no need to adopt as the selection means commonly-used means such as heating, changes in salt concentration and the like which also affect non-specific interactions. Consequently, cleavage can be accomplished, for example, with hardly any change to the conditions for producing specific interaction between the target substance and the functional molecule. Since a functional molecule that has interacted specifically with a specific substance of the present invention will also interact specifically with a target substance that is a constituent of the specific substance, a functional molecule that interacts specifically with a target substance can be manufactured in this way. However, heating or changes in salt concentration can of course be included, if desired owing to one reason or another.

A specific substance of the present invention is derived from a target substance. More specifically, a target substance can be used as it is, if it already has a cleavable linker, while if the target substance lacks a cleavable linker, a specific substance may be a substance comprising the target substance with a cleavable linker added thereto. It may also be a substance comprising a structure other than the cleavable linker added to the target substance in addition to the cleavable linker.

A target substance is not particularly limited as long as it can generate a specific interaction with the functional molecule, and can be selected appropriately according to the object, but preferably it is at least one selected from the proteins, lipoproteins, glycoproteins, polypeptides, lipids, polysaccharides, lipopolysaccharides, nucleic acids and drugs, and of these a plasma protein, tumor marker, apo-protein, virus, autoantibody, coagulation-fibrinolysis factor, hormone, drug in blood, HLA antigen or nucleic acid is preferred. It is particularly desirable that the target substance be a protein.

Examples of the aforementioned plasma proteins include immunoglobulin (IgG, IgA, IgM, IgD, IgE), complement components (C3, C4, C5, C1q), CRP, α1-antitrypsin, α1-microglobulin, β2-microglobulin, haptoglobin, transferrin, ceruloplasmin, ferritin and the like.

Examples of the aforementioned tumor markers include α-fetoprotein (AFP), carcinoembryonic antigen (CEA), CA19-9, CA125, CA15-3, SCC antigen, prostate acid phosphatase (PAP), PIVKA-II, γ-seminoprotein, TPA, elastase I, neuron-specific enolase (NSE), immunosuppressive acidic protein (IAP) and the like.

Examples of the aforementioned apoproteins include apo A-I, apo A-II, apo B, apo C-II, apo C-III, apo E and the like.

Examples of the aforementioned viruses include, for example, the hepatitis B virus (HBV), hepatitis C virus (HBC), HTLV-I, HIV and the like. Examples of non-viral infectious agents include ASO, toxoplasma, mycoplasma, STD and the like.

Examples of the aforementioned autoantibodies include anti-microsome antibodies, anti-thyroglobulin antibodies, anti-nuclear antibodies, rheumatism factors, anti-mitochondrial antibodies, myelin antibodies and the like.

Examples of the aforementioned coagulation-fibrinolysis factors include fibrinogens, fibrin degradation products (FDP), plasminogens, α2-plasmin inhibitors, antithrombin III, β-thromboglobulin, factor VIII, protein C, protein S and the like.

Examples of the aforementioned hormones include pituitary hormones (LH, FSH, GH, ACTH, TSH, prolactin), thyroid hormones (T3, T4, thyroglobulin), calcitonin, parathyroid hormone (PTH), adrenocortical hormones (aldosterone, cortisol), gonadal hormones (hCG, estrogen, testosterone, hPL), pancreatic and digestive tract hormones (insulin, C-peptide, glucagon, gastrin) and others (renin, angiotensin I & II, enkephalins, erythropoietin).

Examples of the aforementioned drugs in blood include carbamazepine, primidone, valproic acid and other anti-epileptic drugs, digoxin, quinidine, digitoxin, theophylline and other circulatory disease drugs, gentamicin, kanamycin, streptomycin and other antibiotics and the like.

Examples of the aforementioned nucleic acids include cancer-associated genes, genes associated with genetic disease, viral genes, bacterial genes and genes exhibiting polymorphisms that are called risk factors for disease.

Examples of the aforementioned cancer-associated genes include the k-ras gene, N-ras gene, p53 gene, BRCA1 gene, BRCA2 gene, src gene, ros gene, APC gene and the like.

Examples of the aforementioned genes associated with genetic disease include those associated, for example, with various congenital metabolic abnormalities such as phenylketonuria, alkaptonuria, cystinuria, Huntington's disease, Down's syndrome, Duchenne's muscular dystrophy, hemophilia and the like.

Examples of the aforementioned viral genes and bacterial genes include those of the hepatitis C virus, hepatitis B virus, influenza virus, measles virus, HIV virus, mycoplasma, *Rickettsia, Streptococcus, Salmonella* and the like.

The aforementioned genes exhibiting polymorphisms are genes the base sequences of which differ from individual to individual without necessarily being a direct cause of disease or the like, including, for example, the PS1 (presenilin 1) genes, PS2 (presenilin 2) genes and APP (beta-amyloid precursor protein) genes, lipoprotein genes, genes associated with HLA (human leukocyte antigen) and blood type, and certain genes thought to be associated with the occurrence of high blood pressure, diabetes and the like.

Examples of substances containing such target substances include bacteria, viruses and other pathogens, blood, sputum, tissue sections and the like isolated from living bodies, and excreta such as feces, urine and the like.

For purposes of pre-natal testing, they also include embryonal cells present in amniotic fluid or part of dividing egg cells in vitro. They may also be cells that have been previously subjected to a cell disruption treatment, for example, with enzymes, heat, surfactants, ultrasound or a combination of these or the like either directly or after having been concentrated as a sediment by centrifugation or the like, as is desired.

A cleavable linker of the present invention, which is a site that is cleavable under a specific condition, can be obtained by binding a substance having a cleavable site to a target substance of the present invention. There are no particular limits on this "substance having a cleavable site" and on the method of binding it to a target substance, and known techniques can be adopted as appropriate.

Specifically, desirable examples of cleavable linkers include those having disulfide bonds or vicinal diol bonds as cleavable sites and those that are cleavable by light. Alternatively, the cleavable linker is preferably a nucleic acid sequence cleavable by a restriction enzyme or an amino acid sequence cleavable by an enzyme.

Figure 1:
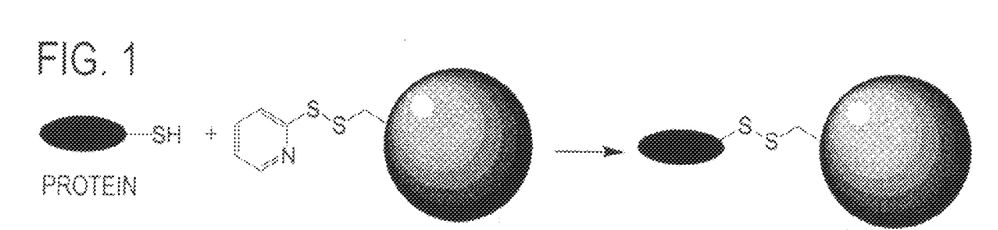
FIG. 1 is a schematic view showing one example in which a disulfide bond is formed with a target substance.
Figure 2:
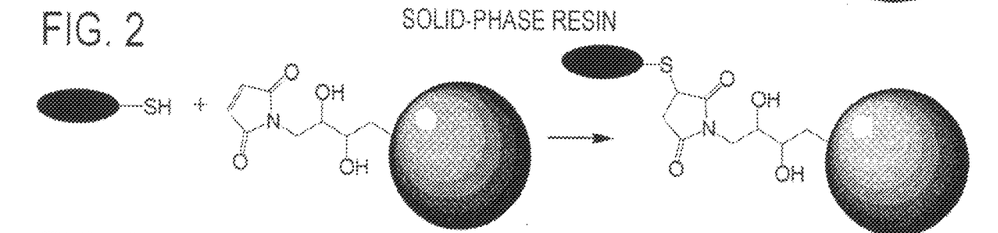
FIG. 2 is a schematic view showing one example in which a vicinal diol bond is formed with a target substance.
Figure 3:
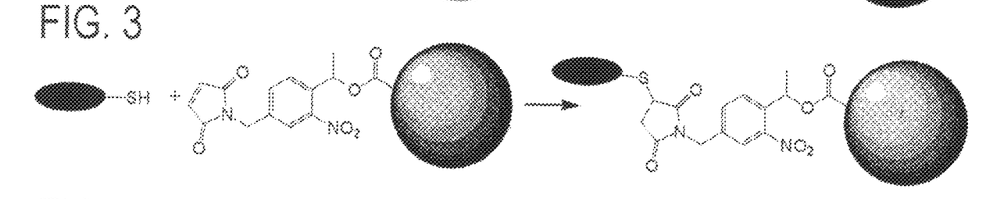
FIG. 3 is a schematic view showing one example in which a light-cleavable bond is formed with a target substance.

An example in which a disulfide bond is formed with a target substance is shown in FIG. 1, while an example in which a vicinal diol bond is formed with a target substance is shown in FIG. 2, and an example in which a light-cleavable bond is formed with a target substance is shown in FIG. 3. In FIGS. 1-3, the protein is the target substance of the present invention, the specific-substance-bound resins of the present invention are shown at the left of the formulae in FIGS. 1-3, and the specific-substance-bound resin with the resin removed is the specific substance of the present invention. In the present invention, obtaining a specific-substance-bound resin by binding a specific substance having a cleavable linker to a resin includes preparing a specific-substance-bound resin by binding to a resin having a cleavable linker as shown here.

An example of a nucleic acid sequence cleavable by a restriction enzyme is an EcoR I recognition sequence such as that represented by the formula given in Example 2, and a protein with an attached cleavable linker can be obtained by synthesizing a terminal amino-modified sequence in a DNA synthesizer, introducing a maleimide group with Sulfo-GMBS and then reacting with the cysteine residue of the protein.

An example of an amino acid sequence cleavable with an enzyme is GFP (Green Fluorescent Protein) having a highly-selective cleavage site (corresponding to the cleavable linker of the present invention), with enterokinase as the enzyme. As is known, enterokinase causes cleavage at AspAspAspAspLys↓. Other enzymes that should have the same effects include Thrombin at LeuValProArg↓GlySer and Factor Xa at IleGluArg↓ from the C-terminal (with ↓ representing the cleavage site). GFP having a highly-selective cleavage site biotinylated via a linker can be easily prepared by genetic recombination using a vector coding for GFP and a Promega PinPoint Xa vector {(http://www.promega.co.jp/lit/pinpoint.htm), Factor Xa cleavable} or Invitrogen pET104-DEST vector {(http://www.invitrogen.co.jp/products/molecular_biology/k104001.pdf}, enterokinase cleavable) or the like, and in fact was prepared using the latter.

The "specific condition" described above means an "established condition," and this "established condition" can be established as desired depending on the cleavable linker, but preferably conditions are selected that maximally exhibit a feature that is "to allow the production of a functional molecule which interacts specifically with a target substance, while suppressing non-specific reactions, without the need to adopt as the selection means commonly-used means such as heating, changes in salt concentration and the like which also affect non-specific interactions," which is a feature of the present invention. In other words, a cleavable linker is preferably selected which allows such a condition to be selected. From the standpoint of avoiding a means that also affects non-specific interactions, the cleavable linker should generally be cleavable at 50° C. or less and in the pH range of 6.0 to 9.0. When the temperature or pH falls outside this range, effects on non-specific interactions become more likely.

There are no particular limits on the resin to be bound with the specific substance or the method of binding with the resin, and known techniques can be adopted as necessary.

In the present invention, the "functional molecule candidates" are substances that may include the functional molecule of the present invention, and consequently include substances other than the functional molecule of the present invention. The molecules that can be used as functional molecules or functional molecule candidates in the present invention are not particularly limited and can be obtained by known methods, but considering the aforementioned target substances they are preferably nucleic acids or modified nucleic acids, and a modified nucleotide n-mer (n≥2) comprising a modified nucleoside having a substituent group introduced into a nucleoside constituting a nucleic acid is more preferred. Furthermore, it is preferable that this functional molecule can be transformed into a nucleic acid when this substituent group is removed by chemical treatment. This is because the possibility of intervention of amplification by the substituent can be eliminated. Such chemical treatment includes any kind of treatment that meets this objective, but in most cases alkali treatment using ammonia water or the like is preferred.

The aforementioned nucleic acid may be either DNA or RNA, and the DNA or RNA may be either single-stranded or double-stranded.

The aforementioned DNA has the four bases adenine (A), thymine (T), guanine (G) and cytosine (C), and in the DNA polynucleotide chain these bases extend inward towards each other in planes perpendicular to the central axis, forming so-called Watson-Crick base pairs, with adenine specifically bound to thymine and guanine specifically bound to cytosine, respectively, by hydrogen bonds. As a result, two polypeptide chains are bound together complementarily in the aforementioned double-stranded DNA.

The four nucleosides (deoxyribonucleosides) of the aforementioned DNA may be deoxyadenosine (dA), deoxyguanosine (dG), deoxycytidine (dC) and deoxythymidine (dT).

The aforementioned RNA has the four bases adenine (A), thymine (T), uracil (U) and cytosine (C), and is broadly categorized into three types: ribosome RNA (rRNA), transfer RNA (tRNA) and messenger RNA (mRNA).

The four nucleosides (ribonucleosides) of the aforementioned RNA may be adenosine (A), guanosine (G), cytidine (C) and uridine (U).

The aforementioned modified nucleotide dimer comprising a modified nucleoside having an introduced substituent group may be a combination of a modified nucleoside with the aforementioned 4 nucleosides constituting the nucleic acid, or may be a combination of modified nucleosides. The substituent group may also be introduced into a nucleotide (nucleoside with a phosphoric acid group added) rather than into a nucleoside (purine or pyrimidine base with a sugar linked thereto).

The position at which the substituent group is introduced in the aforementioned modified nucleoside is not particularly limited and can be selected appropriately according to the object, with examples including pyrimidine 5-position, purine 7-position, purine 8-position and exocyclic amine substitution, 4-thiouridine substitution, 5-bromo or 5-iodo-uracil substitution and the like, but from the standpoint of preventing enzyme reactions during amplification introduction is preferably into the pyrimidine 5-position.

The method for introducing a substituent group into a nucleoside is not particularly limited and can be selected appropriately according to the object, but, for example, a method of introducing a substituent group into the pyrimidine 5-position as shown below is desirable.

Deoxyuridine

Deoxyuridine derivative

Deoxyuridine relative

Deoxycytosine derivative

Deoxycytosine relative

In the formulae, the substituent group R is a natural or artificial amino acid substituent group, metal complex, fluorescent dye, oxidation-reduction dye, spin-labeled material or group represented by (1) through (10) below or the like.

(1)

(2)

(3)

(4)

(5)

(6)

(7)

(8)

(9)

(10)

The method of synthesizing a modified nucleotide dimer comprising this modified nucleoside is not particularly limited and can be selected appropriately according to the object, but examples include the diester method, triester method, phosphite method, phosphoramidite method, H-phosphonate method, thiophosphate method and the like, and of these the phosphoramidite method is preferred.

In general, the key reaction in the phosphoramidite method is a condensation reaction of a nucleoside phosphoramidite and a nucleoside using tetrazole as the accelerator. This reaction normally acts competitively on both the hydroxyl groups of the sugar part and the amino groups of the nucleoside base part, but for purposes of nucleotide synthesis which is desired it is made to act selectively only on the hydroxyl groups of the sugar part. Consequently, protective groups are added for modification in order to prevent side reactions involving the amino groups.

For example, a modified nucleotide dimer (AU1) can be synthesized from deoxyadenosine and a modified deoxyuridine as shown by the following formulae:

Deoxyadenosine

Modified deoxyuridine ($U_1$)

-continued

Phosphoramidite (AU₁)

(wherein DMTr represents a dimethoxytrityl group).

Trimers and higher modified nucleotide n-mers can be prepared by similar methods. There is no particular upper limit on n, and oligomers and polymers are included. In many cases n is preferably 10 to 50.

In the present invention, a "solution comprising functional molecule candidates" is a solution that is thought to comprise such a functional molecule, and can be defined specifically as desired. There are no particular limits on the solvent used here, and a known solvent can be used. "Treatment in a solution comprising functional molecule candidates" here signifies that a resin with a specific substance bound thereto is brought into contact with a solution comprising functional molecule candidates. If the functional molecule is included in the functional molecule candidates, the specific substance and functional molecule will interact specifically as a result of this treatment.

Next, the cleavable linker is cleaved under the aforementioned specific condition to select the functional molecule. In this way, it is possible to manufacture a functional molecule that interacts specifically with a target substance while controlling non-specific reactions, without the need to adopt means which also affect non-specific interactions. However, of course heating and changes in salt concentration can also be included if desired owing to one reason or another.

Figure 4:
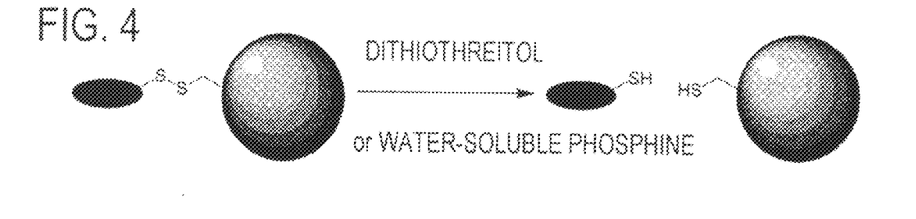
FIG. 4 is s schematic view showing one example in which cleavage of a disulfide bond of a specific substance occurs.
Figure 5:
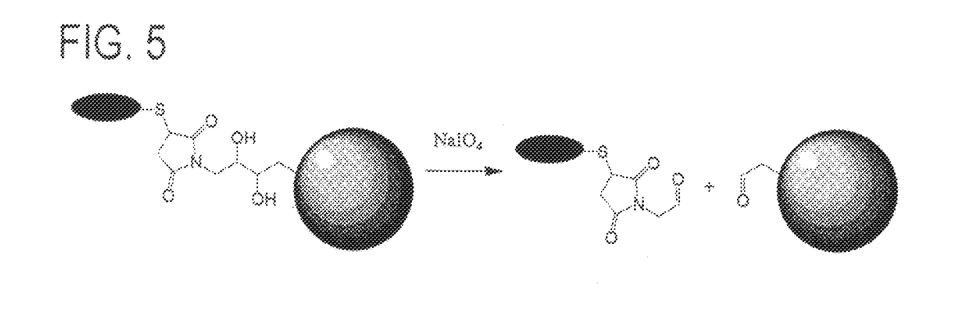
FIG. 5 is a schematic view showing one example in which cleavage of a vicinal diol bond of a specific substance occurs.
Figure 6:
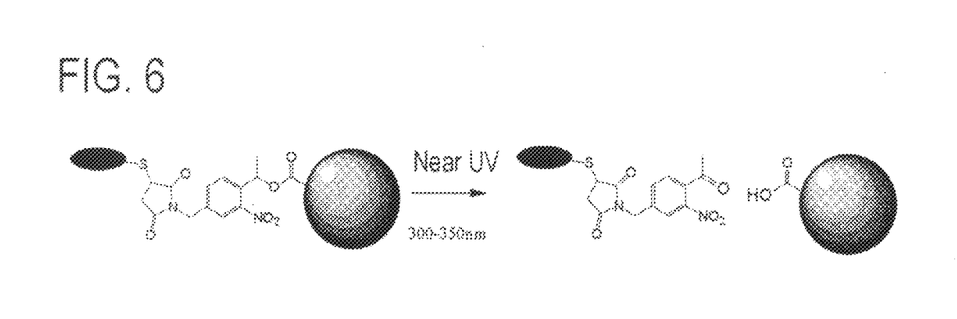
FIG. 6 is a schematic view showing one example in which cleavage of a specific substance with light occurs.

An example of cleaving the disulfide bonds of a specific substance is shown in FIG. 4, while an example of cleaving the vicinal diol bonds of a specific substance is shown in FIG. 5, and an example of cleaving a specific substance by light is shown in FIG. 6. The ovals and circles in the figures have the same meaning as in FIGS. 1-3.

Affinity chromatography is preferably adopted for selecting functional molecules. Affinity chromatography is a means of isolation and purification using the biological affinity of specific components that bind easily to one another. In detail, a specific substance is fixed to a resin or other column filler and equilibrated with a buffer solution for binding, after which a solution comprising functional molecule candidates (such as oligonucleotide sequences) is poured into the column and left under a fixed condition, and since an oligonucleotide sequence capable of specific interaction with the specific substance is adsorbed by the column, components other than the residual oligonucleotide sequence can be removed by thoroughly washing with a buffer solution for binding. The aforementioned specific condition is then established within the affinity chromatography system, the cleavable linker is cleaved, the oligonucleotide sequence which is kept as being interacted specifically with the aforementioned specific substance which has now lost its cleaved linker site is filtered out, and this oligonucleotide sequence is the functional molecule of the present invention. Other known purification methods can also be included for further selection of the functional molecule, and such cases are included in the scope of the present invention.

The functional molecule synthesized by the present invention could be, for example, a multifunctional drug or substance for highly precise drug delivery if a functional molecule is identified that is capable of specific interaction with a protein involved in a particular metabolic system. If a functional molecule is identified that is capable of specifically interacting with a specific DNA sequence, it is expected that it could be used to control the expressed amounts of a series of genes or to elucidate the interactions of gene products. Moreover, if a molecule is identified that is capable of interacting specifically with a molecule that mimics a reaction intermediate, it could be used to more efficiently accomplish multi-stage reactions involving unstable reaction intermediates. A functional molecule could also be attached or bound to a crystal oscillator or surface acoustic wave element and used as a biosensor.

EXAMPLES

Examples of the present invention are explained in detail below.

Example 1

Preparation of a DNA Random Mix

Figure 7:
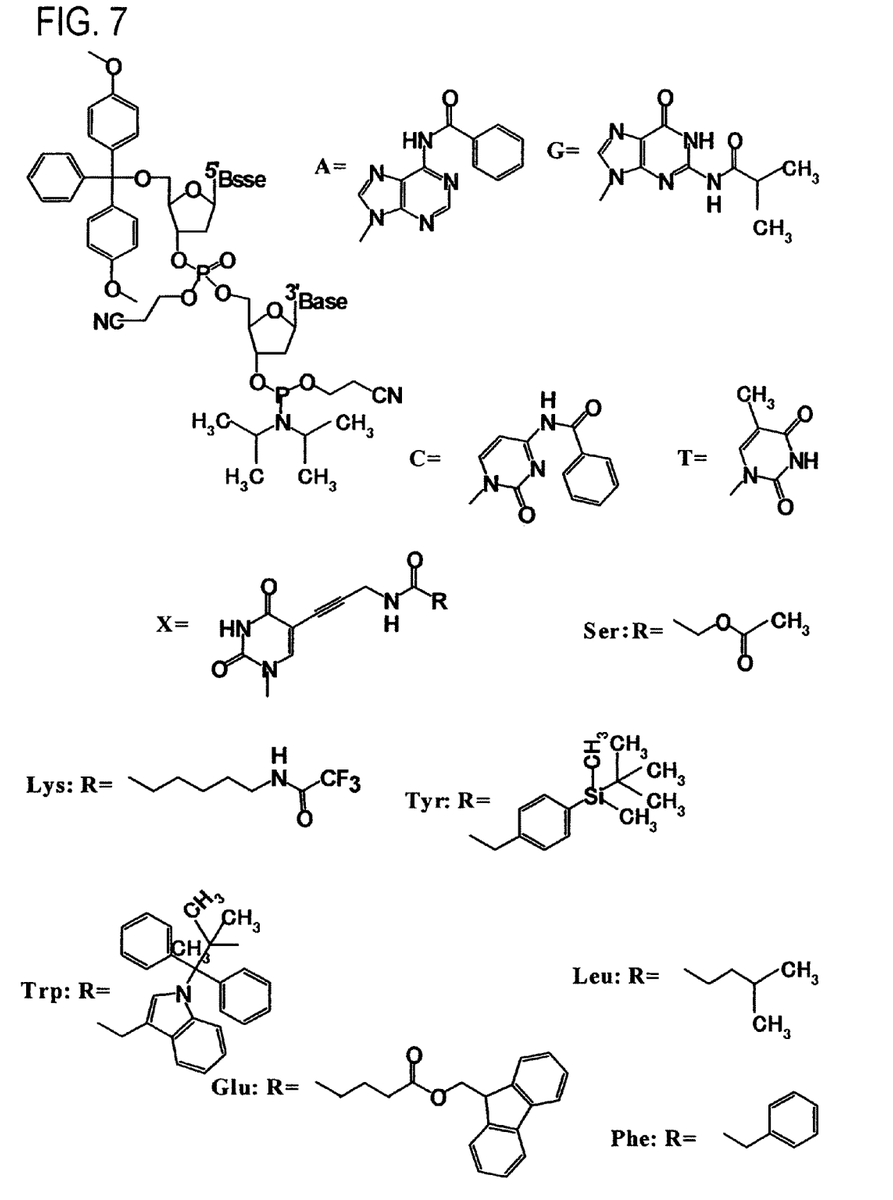
FIG. 7 is for purposes of explaining the structures represented by the various symbols in Table 1.

A DNA random mix was synthesized using techniques similar to those used in the prior application. Specifically, a DNA random mix with the structure tta tcaacaaaat actccaattg (NpNp)$_{25}$ga aagatcccaacgaaaag (SEQ ID No. 1) was synthesized in an automatic DNA synthesizer (Applied 391A). The NpNp part was synthesized using a mixture (random mix) of dimer amidites combined as in Table 1. In Table 1, the combinations with the strike-out lines are not included. The structures represented by abbreviations in Table 1 are summarized in FIG. 7. FIG. 7 is read as follows. That is, the structure of the dimer amidites of Table 1 is shown at the upper left of FIG. 7, with A, G, C, T and X structures for the 3' Base and 5' Base. Lys means that the R in the structure represented by X has the structure represented by Lys:R in FIG. 7. The same applies to Tyr, Trp, Leu, Glu, Phe and Ser. For example, in Table 1 Lys is given in the box at the intersection of A (3') and X (5') in reference to FIG. 7, and this means that in the dimer amidite structure at the upper left of FIG. 7, the 3' Base has the A structure of FIG. 7, the 5' base has the X structure of FIG. 7, and the R in X has a Lys structure.

TABLE 1

|    |   | 3' |   |   |   |   |
|----|---|----|---|---|---|---|
|    |   | A  | G | C | T | X |
| 5' | A |    |   |   |   | Leu |
|    | G |    |   |   |   | Glu |
|    | C |    |   |   |   | Phe |
|    | T |    |   |   |   | Ser |
|    | X | Lys | Tyr | Trp |   |   |

The synthesized DNA random mix was excised from the resin using aqueous ammonia, and then deprotected.

(Selection of a Functional Molecule)

A streptavidin resin was impregnated with a solution of biotin-modified (biotinylated) GFP (Green Fluorescent Protein) having an enterokinase cleavage site (corresponding to a cleavable linker of the present invention) between the biotin-modified site and the protein itself, and washed to prepare a GFP-bound resin.

Next, 200 μL (50 nmol) of the aforementioned DNA random mix was reacted overnight at room temperature to prepare a modified nucleic acid-GFP-streptavidin-biotin modified resin, and washed 10 times or more at 50° C. each time with 1 mL of a mixed solution of NaCl (10 mM), MgCl$_2$ (1 mM) and Tris-HCl (10 mM, pH=8.5). Thorough washing was confirmed by the absence of the modified nucleic acid in the wash liquid, which was checked by quantitative PCR.

This resin was then reacted with enterokinase to cleave the enterokinase cleavage site {corresponding to "cleaving a cleavable linker under a specific condition" using an enzyme (enterokinase) in the present invention}, and the GFP outflow was confirmed from the fluorescence.

Using the resulting solution containing GFP, PCR was performed using the primers TTATCAACAAAATACTC-CAATTG (SEQ ID No. 2) and CTTTTCGT-TGGGATCTTTC (SEQ ID No. 3) to amplify the DNA. The product was cloned, and 100 clones were sequenced. DNA was thus obtained having Lys, Tyr, Trp, Leu, Glu, Phe and Ser replaced by T.

Then, these were decoded by block coding to discover the structure of the DNA with T restored to Lys, Tyr, Trp, Leu, Glu, Phe and Ser, the modified nucleic acids were synthesized in an automatic DNA synthesizer, and the dissociation constants of the binding of each of them with GFP were determined. As a result, 10 of the resulting sequences were confirmed to have Kd=$10^{-7}$ or less.

Meanwhile, DNA sequences eluted by raising the temperature rather than with enterokinase were sequenced in the same way using 100 clones. These were decoded by block coding, modified nucleic acids were synthesized with an automatic DNA synthesizer, and the dissociation constants of the binding of each of them with GFP were determined, but only 1 sequence was confirmed to have Kd=$10^{-7}$ or less.

These results show that in the method for manufacturing a functional molecule using a cleavable linker of the present invention, nonspecific interactions can be effectively excluded from a system including various types of modified nucleic acids, unlike in methods in which DNA sequences are isolated simply by raising the temperature.

Example 2

GFP having a cysteine residue introduced site-specifically by genetic manipulation was reacted with a DNA of the following formula (SEQ ID No. 4) which had been biotin-modified and modified with a terminal maleimide group, and a GFP-DNA complex was isolated having GFP bound to this DNA (corresponding to a cleavable linker of the present invention).

5' Base is A, the 3' Base is X and the R thereof is Leu in the structure at the upper left of FIG. 7.

The DNA random mix described above was synthesized on resin, separated from the resin by phosphine treatment and then deprotected.

Next, a GFP-bound resin prepared as in Example 1 was reacted overnight at room temperature with 80 μL (560 pmol) of this DNA random mix to prepare a modified nucleic acid-GFP-enterokinase recognition site-biotin-streptavidin resin (complex resin).

This complex resin was washed and verified as in Example 1.

Next, a modified nucleic acid-GFP-streptavidin-biotin modified resin was prepared as in Example 1 using this GFP-DNA complex, and washed 10 times or more at 50° C. each time with 1 mL of a mixed solution of NaCl (50 mM), $MgCl_2$ (1 mM), Tween-20 (0.05%) and Tris-HCl (10 mM, pH=8.5). Thorough washing was confirmed by the absence of the modified nucleic acid in the wash liquid, which was checked by quantitative PCR.

This was washed in advance with GCTCATGAAT-TCTAATCGTAGT (SEQ ID No. 5) and further with the EcoR I cleavage buffer solution. Next, the complementary strand of this DNA was poured on the resin to form a double strand, an EcoR I solution was also poured to cleave this double strand with EcoR I (corresponding to "cleaving a cleavable linker under a specific condition" using a restriction enzyme (EcoR I) in the present invention), and the GFP outflow was confirmed from the fluorescence.

Using the resulting solution containing GFP, PCR was performed using the primers TTATCAACAAAATACTC-CAATTG (SEQ ID No. 2) and CTTTTCGT-TGGGATCTTTC (SEQ ID No. 3) to amplify the DNA. The product was cloned, and 100 clones were sequenced.

These were decoded by block decoding, modified nucleic acids were synthesized in an automatic DNA synthesizer, and the dissociation constants of the binding of each of them with GFP were determined. As a result, 15 sequences were confirmed to have Kd=$10^{-7}$ or less.

Meanwhile, DNA sequences eluted by raising the temperature were sequenced in the same way using 100 clones. These were decoded by block coding, modified nucleic acids were synthesized with an automatic DNA synthesizer, and the dissociation constants of the binding of each of them with GFP were determined, but no sequence was confirmed to have Kd=$10^{-7}$ or less.

Example 3

Preparation of a DNA Random Mix

A DNA random mix was synthesized by the same methods as in Example 1. Specifically, a DNA random mix with a 5'-gaaggtgaaggtcggagtcaacg((NPNP)g/c)$_7$gct((NPNP)g/c)$_7$ggaaatcccat caccatcttc-3' (SEQ ID No. 6) structure was synthesized in an automatic DNA synthesizer. The NpNp part was any of dALeu-dA, dAPhe-dC, dAGlu-dT, dGly-dC and dT-dALys. Here, dALeu-dA for example means that the (Biotin Tag Cleavage with Enterokinase and Sequence Analysis of Modified Nucleic Acids)

The complex resin was equilibrated with 20 mM Tris-HCl (pH 7.4), 50 mM KCl and 2 mM $CaCl_2$, and 1 unit of enterokinase was added and reacted overnight at 20° C. Upon completion of the reaction, the solution was filtered to separate and collect the resin and the modified nucleic acid-GFP complex.

Ammonia water (alkali treatment agent, one of chemical treatments of the present invention) was added to the modified nucleic acid-GFP solution, and reacted for 2 hours at 70° C. to remove the nucleic acid modifying portion (that is, the substituent group of the present invention). The water was completely removed by pressure reducing treatment, and the resulting nucleic acid was dissolved in a buffer for polymerase (Pfu DNA polymerase obtained from Toyobo Co.) in accordance with the attached protocols. When PCR was performed with a PCR unit using 5'-GAAGGT-GAAGGTCGGAGTCAACG-3' (SEQ ID No. 7) and 5'-GAAGATGGTGATGGGATTTCC-3' (SEQ ID No. 8) as the primers to amplify the collected nucleic acid, they were amplified without difficulty.

When the amplified PCR product was verified by agarose electrophoresis, it was confirmed that a DNA fragment of the proper length in comparison with the size of a DNA marker (Invitrogen, 25 bp ladder) had been amplified. The PCR product was ligated to the cloning vector pCR-BluntII-TOPO, and introduced into E. coli. The transformed E. coli was applied to LB agar medium containing kanamycin, and cultured at 37° C. Single colonies were picked out and cultured separately, and the respective plasmids were extracted and purified. The cloned sequences of 100 of the resulting plasmids were analyzed.

The resulting sequence information was decoded by block coding to determine the structure, the modified nucleic acid with the modified information restored were synthesized with an automatic DNA synthesizer, and the dissociation constants with GFP were determined.

(Measurement and Calculation of Dissociation Constants)

The binding dissociation constants (KD) with respect to GFP were determined using AQUA (Initium Co. software from the results of equilibrium analysis measurement by the saturation method using a quartz crystal microbalance (Initium Co.).

Specifically, 2 μL of GFP solution (10 μg/mL) was brought into contact with the gold surface of the crystal oscillator, and air-dried to fix the GFP. The GFP-fixed crystal oscillator was attached to an apparatus (quartz crystal microbalance), and immersed in a 1.6 mL reaction tank filled with TBS (Tris buffered saline). After the sensorgram had stabilized, modified nucleic acid with a final concentration of 0.5 µM was added to the reaction tank, and mass increase on the crystal oscillator was monitored.

Figure 8:
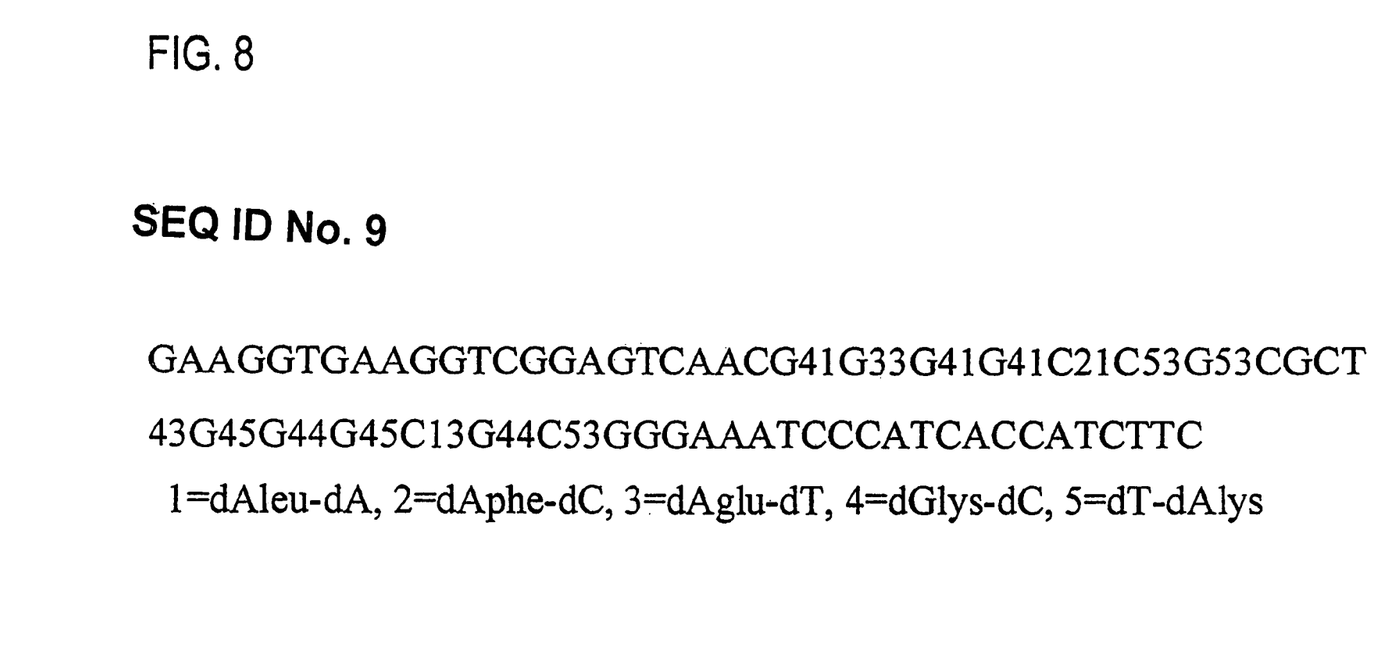
FIG. 8 shows the sequence of the modified nucleic acid used to obtain the sensorgram of FIG. 9.
Figure 9:
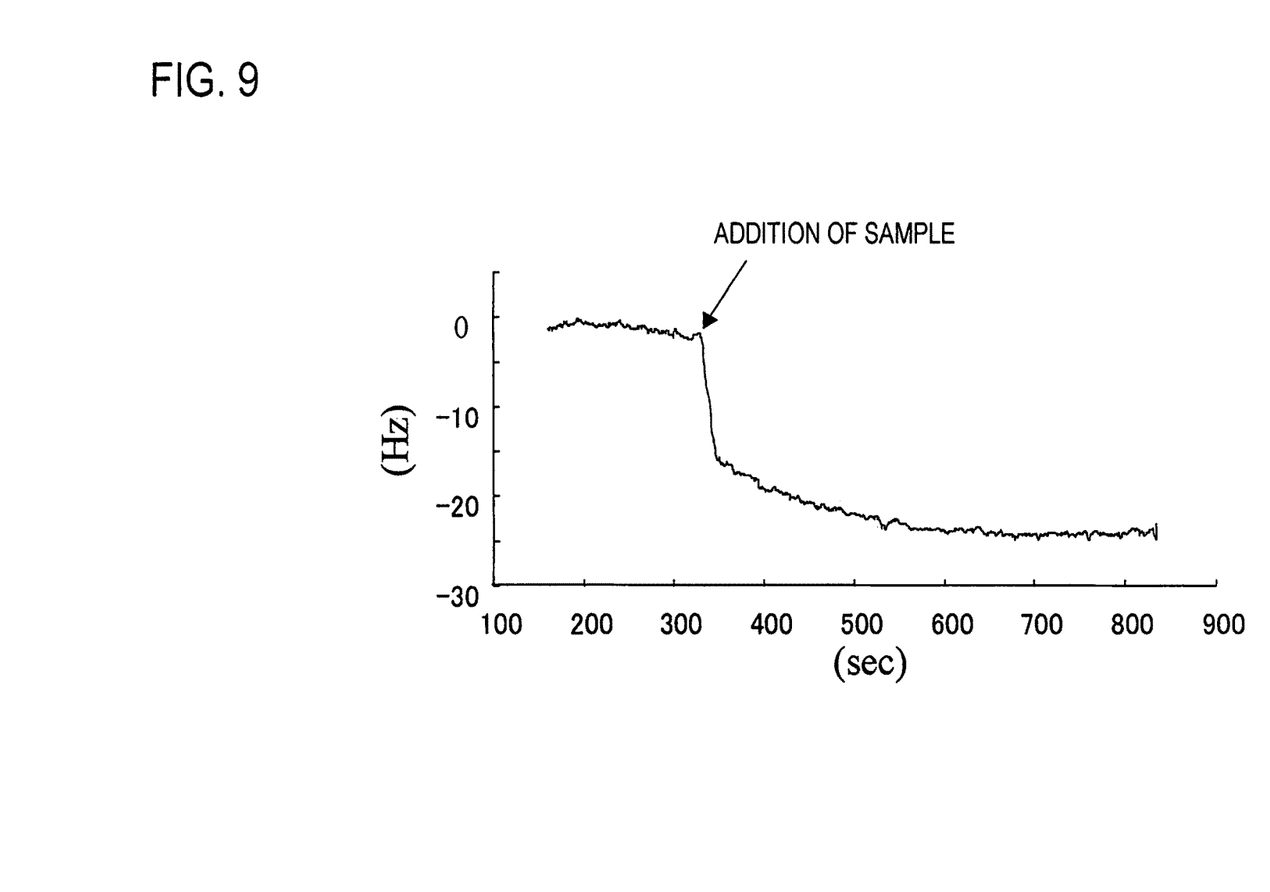
FIG. 9 shows a sensorgram of the modified nucleic acid of FIG. 8.

Of the nucleic acid, a sensorgram such as that shown in FIG. 9 was obtained from such measurement of a modified nucleic acid having the sequence shown in FIG. 8 (SEQ ID No. 9). Equilibrium analysis was also performed by the saturation method. When the resulting data was processed by AQUA, the KD was calculated as $3.08 \times 10^{-6}$.

What is claimed is:

1. A method for manufacturing a functional molecule, comprising:

taking a solution comprising functional molecule candidates wherein said functional molecule candidate is a modified nucleotide n-mer (n>=2) comprising a modified nucleoside having a substituent group, and wherein said functional molecule can be transformed into a nucleic acid when said substituent group is removed by alkali treatment;

binding, to a resin, a specific substance having a cleavable linker which is a site that is cleavable under a specific condition to prepare a specific-substance-bound resin;

treating said specific-substance-bound resin with said solution comprising said functional molecule candidates;

cleaving said cleavable linker under said specific condition and selecting a functional molecule which has interacted specifically with said specific substance;

removing said substituent group of said functional molecule by alkali treatment to produce a nucleic acid; and identifying said nucleic acid, thereby identifying said functional molecule wherein said functional molecule candidate is a modified nucleotide n-mer (n>=2) comprising a modified nucleoside having the substituent group attached to a nucleotide base.

2. The manufacturing method according to claim 1, wherein said cleavable linker is cleavable at 50° C. or less and in the pH range of 6.0 to 9.0.

3. The manufacturing method according to claim 1, wherein the substituent group is attached to a pyrimidine 5-position, a purine 7-position or a purine 8-position.

4. The manufacturing method according to claim 3, wherein the substituent group is attached to a pyrimidine 5-position.

5. The manufacturing method according to claim 3, wherein the substituent group is attached to a purine 7-position.

6. The manufacturing method according to claim 1, wherein said cleavable linker has disulfide bonds, vicinal diol bonds or is cleavable by light.

7. The manufacturing method according to claim 6, wherein said cleavable linker has disulfide bonds.

8. The manufacturing method according to claim 1, wherein said cleavable linker is a nucleic acid sequence cleavable with a restriction enzyme or an amino acid sequence cleavable by an enzyme.

9. The manufacturing method according to claim 1 wherein n is 10 to 50.

* * * * *

SEQUENCE LISTING

```
<160> NUMBER OF SEQ ID NOS: 9

<210> SEQ ID NO 1
<211> LENGTH: 92
<212> TYPE: DNA
<213> ORGANISM: Artificial Sequence
<220> FEATURE:
<223> OTHER INFORMATION: made in lab
<220> FEATURE:
<221> NAME/KEY: modified_base
<222> LOCATION: (24)..(73)
<223> OTHER INFORMATION: a, g, c, t or a modified base

<400> SEQUENCE: 1
ttatcaacaa aatactccaa ttgnnnnnnn nnnnnnnnnn nnnnnnnnnn nnnnnnnnnn      60
nnnnnnnnnn nnngaaagat cccaacgaaa ag                                   92

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
ttatcaacaa aatactccaa ttg                                             23

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
cttttcgttg ggatctttc                                                  19

<210> SEQ ID NO 4
<211> LENGTH: 22
<212> TYPE: DNA
<213> ORGANISM: Artificial Sequence
<220> FEATURE:
<223> OTHER INFORMATION: made in lab
<220> FEATURE:
<221> NAME/KEY: misc_difference
<222> LOCATION: (1)..(1)
<223> OTHER INFORMATION: 5'-maleimide modified dG
<220> FEATURE:
<221> NAME/KEY: misc_difference
<222> LOCATION: (22)..(22)
<223> OTHER INFORMATION: 3' biotinylated T

<400> SEQUENCE: 4
nctcatgaat tctaatcgta gn                                              22

<210> SEQ ID NO 5
<211> LENGTH: 22
<212> TYPE: DNA
<213> ORGANISM: Artificial Sequence
<220> FEATURE:
```

```
<223> OTHER INFORMATION: primer

<400> SEQUENCE: 5
gctcatgaat tctaatcgta gt                                              22

<210> SEQ ID NO 6
<211> LENGTH: 117
<212> TYPE: DNA
<213> ORGANISM: Artificial Sequence
<220> FEATURE:
<223> OTHER INFORMATION: made in lab
<220> FEATURE:
<221> NAME/KEY: modified_base
<222> LOCATION: (24)..(27)
<223> OTHER INFORMATION: a, g, c, t or a modified base
<220> FEATURE:
<221> NAME/KEY: modified_base
<222> LOCATION: (29)..(32)
<223> OTHER INFORMATION: a, g, c, t or a modified base
<220> FEATURE:
<221> NAME/KEY: modified_base
<222> LOCATION: (34)..(37)
<223> OTHER INFORMATION: a, g, c, t or a modified base
<220> FEATURE:
<221> NAME/KEY: modified_base
<222> LOCATION: (39)..(42)
<223> OTHER INFORMATION: a, g, c, t or a modified base
<220> FEATURE:
<221> NAME/KEY: modified_base
<222> LOCATION: (44)..(47)
<223> OTHER INFORMATION: a, g, c, t or a modified base
<220> FEATURE:
<221> NAME/KEY: modified_base
<222> LOCATION: (49)..(52)
<223> OTHER INFORMATION: a, g, c, t or a modified base
<220> FEATURE:
<221> NAME/KEY: modified_base
<222> LOCATION: (54)..(57)
<223> OTHER INFORMATION: a, g, c, t or a modified base
<220> FEATURE:
<221> NAME/KEY: modified_base
<222> LOCATION: (62)..(65)
<223> OTHER INFORMATION: a, g, c, t or a modified base
<220> FEATURE:
<221> NAME/KEY: modified_base
<222> LOCATION: (67)..(70)
<223> OTHER INFORMATION: a, g, c, t or a modified base
<220> FEATURE:
<221> NAME/KEY: modified_base
<222> LOCATION: (72)..(75)
<223> OTHER INFORMATION: a, g, c, t or a modified base
<220> FEATURE:
<221> NAME/KEY: modified_base
<222> LOCATION: (77)..(80)
<223> OTHER INFORMATION: a, g, c, t or a modified base
<220> FEATURE:
<221> NAME/KEY: modified_base
<222> LOCATION: (77)..(80)
<223> OTHER INFORMATION: a, g, c, t or a modified base
<220> FEATURE:
<221> NAME/KEY: modified_base
<222> LOCATION: (82)..(85)
<223> OTHER INFORMATION: a, g, c, t or a modified base
<220> FEATURE:
<221> NAME/KEY: modified_base
<222> LOCATION: (87)..(90)
<223> OTHER INFORMATION: a, g, c, t or a modified base
<220> FEATURE:
<221> NAME/KEY: modified_base
<222> LOCATION: (92)..(95)
<223> OTHER INFORMATION: a, g, c, t or a modified base

<400> SEQUENCE: 6
gaaggtgaag gtcggagtca acgnnnnsnn nnsnnnnsnn nnsnnnnsnn nnsnnnnsgc      60
tnnnnsnnnn snnnnsnnnn snnnnsnnnn snnnnsggaa atcccatcac catcttc        117
```

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gaaggtgaag gtcggagtca acg                                           23

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gaagatggtg atgggatttc c                                             21

<210> SEQ ID NO 9
<211> LENGTH: 117
<212> TYPE: DNA
<213> ORGANISM: Artificial Sequence
<220> FEATURE:
<223> OTHER INFORMATION: made in lab
<220> FEATURE:
<221> NAME/KEY: modified_base
<222> LOCATION: (24)..(24)
<223> OTHER INFORMATION: a, g, c, t or a modified base
<220> FEATURE:
<221> NAME/KEY: modified_base
<222> LOCATION: (26)..(26)
<223> OTHER INFORMATION: a, g, c, t or a modified base
<220> FEATURE:
<221> NAME/KEY: modified_base
<222> LOCATION: (29)..(29)
<223> OTHER INFORMATION: a, g, c, t or a modified base
<220> FEATURE:
<221> NAME/KEY: modified_base
<222> LOCATION: (31)..(31)
<223> OTHER INFORMATION: a, g, c, t or a modified base
<220> FEATURE:
<221> NAME/KEY: modified_base
<222> LOCATION: (34)..(34)
<223> OTHER INFORMATION: a, g, c, t or a modified base
<220> FEATURE:
<221> NAME/KEY: modified_base
<222> LOCATION: (36)..(36)
<223> OTHER INFORMATION: a, g, c, t or a modified base
<220> FEATURE:
<221> NAME/KEY: modified_base
<222> LOCATION: (39)..(39)
<223> OTHER INFORMATION: a, g, c, t or a modified base
<220> FEATURE:
<221> NAME/KEY: modified_base
<222> LOCATION: (41)..(41)
<223> OTHER INFORMATION: a, g, c, t or a modified base
<220> FEATURE:
<221> NAME/KEY: modified_base
<222> LOCATION: (44)..(44)
<223> OTHER INFORMATION: a, g, c, t or a modified base
<220> FEATURE:
<221> NAME/KEY: modified_base
<222> LOCATION: (46)..(46)
<223> OTHER INFORMATION: a, g, c, t or a modified base
<220> FEATURE:
<221> NAME/KEY: modified_base
<222> LOCATION: (50)..(50)
<223> OTHER INFORMATION: a, g, c, t or a modified base
<220> FEATURE:
<221> NAME/KEY: modified_base
<222> LOCATION: (51)..(51)

```
<223> OTHER INFORMATION: a, g, c, t or a modified base
<220> FEATURE:
<221> NAME/KEY: modified_base
<222> LOCATION: (55)..(55)
<223> OTHER INFORMATION: a, g, c, t or a modified base
<220> FEATURE:
<221> NAME/KEY: modified_base
<222> LOCATION: (56)..(56)
<223> OTHER INFORMATION: a, g, c, t or a modified base
<220> FEATURE:
<221> NAME/KEY: modified_base
<222> LOCATION: (62)..(62)
<223> OTHER INFORMATION: a, g, c, t or a modified base
<220> FEATURE:
<221> NAME/KEY: modified_base
<222> LOCATION: (64)..(64)
<223> OTHER INFORMATION: a, g, c, t or a modified base
<220> FEATURE:
<221> NAME/KEY: modified_base
<222> LOCATION: (67)..(67)
<223> OTHER INFORMATION: a, g, c, t or a modified base
<220> FEATURE:
<221> NAME/KEY: modified_base
<222> LOCATION: (70)..(70)
<223> OTHER INFORMATION: a, g, c, t or a modified base
<220> FEATURE:
<221> NAME/KEY: modified_base
<222> LOCATION: (72)..(72)
<223> OTHER INFORMATION: a, g, c, t or a modified base
<220> FEATURE:
<221> NAME/KEY: modified_base
<222> LOCATION: (74)..(74)
<223> OTHER INFORMATION: a, g, c, t or a modified base
<220> FEATURE:
<221> NAME/KEY: modified_base
<222> LOCATION: (77)..(77)
<223> OTHER INFORMATION: a, g, c, t or a modified base
<220> FEATURE:
<221> NAME/KEY: modified_base
<222> LOCATION: (80)..(80)
<223> OTHER INFORMATION: a, g, c, t or a modified base
<220> FEATURE:
<221> NAME/KEY: modified_base
<222> LOCATION: (82)..(82)
<223> OTHER INFORMATION: a, g, c, t or a modified base
<220> FEATURE:
<221> NAME/KEY: modified_base
<222> LOCATION: (84)..(84)
<223> OTHER INFORMATION: a, g, c, t or a modified base
<220> FEATURE:
<221> NAME/KEY: modified_base
<222> LOCATION: (87)..(87)
<223> OTHER INFORMATION: a, g, c, t or a modified base
<220> FEATURE:
<221> NAME/KEY: modified_base
<222> LOCATION: (89)..(89)
<223> OTHER INFORMATION: a, g, c, t or a modified base
<220> FEATURE:
<221> NAME/KEY: modified_base
<222> LOCATION: (93)..(93)
<223> OTHER INFORMATION: a, g, c, t or a modified base
<220> FEATURE:
<221> NAME/KEY: modified_base
<222> LOCATION: (94)..(94)
<223> OTHER INFORMATION: a, g, c, t or a modified base

<400> SEQUENCE: 9
gaaggtgaag gtcggagtca acgncnagnt ntgncnagnc nacncnactn ntgtnntcgc      60
tncntgnctn gncncgnctn cnantgncnc ctnntgggaa atcccatcac catcttc        117
```